(12) United States Patent
Couture et al.

(10) Patent No.: US 11,583,224 B2
(45) Date of Patent: Feb. 21, 2023

(54) METHOD AND SYSTEM FOR TRACKING TOOLS IN COMPUTER-ASSISTED SURGERY

(71) Applicant: ORTHOSOFT ULC, Montreal (CA)

(72) Inventors: Pierre Couture, Montreal (CA); Sebastien Jutras, Montreal (CA)

(73) Assignee: ORTHOSOFT ULC, Montreal (CA)

( * ) Notice: Subject to any disclaimer, the term of this patent is extended or adjusted under 35 U.S.C. 154(b) by 333 days.

(21) Appl. No.: 16/944,313

(22) Filed: Jul. 31, 2020

(65) Prior Publication Data
US 2020/0359957 A1 Nov. 19, 2020

Related U.S. Application Data

(63) Continuation of application No. 11/688,951, filed on Mar. 21, 2007, now Pat. No. 10,765,356.
(Continued)

(51) Int. Cl.
*A61B 5/00* (2006.01)
*A61B 34/20* (2016.01)
(Continued)

(52) U.S. Cl.
CPC ............ *A61B 5/4504* (2013.01); *A61B 5/103* (2013.01); *A61B 34/20* (2016.02); *A61B 90/36* (2016.02);
(Continued)

(58) Field of Classification Search
CPC ....... A61B 5/4504; A61B 5/103; A61B 34/20; A61B 2034/102; A61B 2034/105
See application file for complete search history.

(56) References Cited

U.S. PATENT DOCUMENTS 6,450,978 B1 9/2002 Brosseau et al.
6,533,737 B1 3/2003 Brosseau et al.
(Continued)

FOREIGN PATENT DOCUMENTS

EP 1679047 A2 7/2006
WO 2003068078 A1 8/2003
(Continued)

OTHER PUBLICATIONS

U.S. Appl No. 60/682,852, filed May 20, 2005, Pelletier et al.
(Continued)

*Primary Examiner* — Jason M Ip
(74) *Attorney, Agent, or Firm* — Norton Rose Fulbright Canada LLP

(57) ABSTRACT

A system for tracking a bone-altering tool in computer-assisted surgery, comprising a first trackable reference secured to a first bone, with a first frame of reference being associated with the first trackable reference. A bone-altering tool is securable to the first bone in a secured configuration. Sensors track the trackable reference for position and orientation. A position/orientation calculator is connected to the sensor device to calculate a position and orientation of the first frame of reference. An alteration parameter calculator is associated with the position/orientation calculator to determine a position and orientation of the bone-altering tool in the secured configuration as a function of the position and orientation of the first frame of reference and of the secured configuration. A method for tracking tools using the tracking of a bone is provided.

18 Claims, 4 Drawing Sheets

Related U.S. Application Data

(60) Provisional application No. 60/784,789, filed on Mar. 23, 2006.

(51) Int. Cl.
*A61B 34/10* (2016.01)
*A61B 34/00* (2016.01)
*A61B 5/103* (2006.01)
*A61B 90/00* (2016.01)

(52) U.S. Cl.
CPC ... *A61B 2034/102* (2016.02); *A61B 2034/105* (2016.02); *A61B 2034/256* (2016.02)

(56) References Cited

U.S. PATENT DOCUMENTS

| | | |
|---|---|---|
| 6,917,827 B2 | 7/2005 | Kienzle, III |
| 7,885,705 B2 | 2/2011 | Murphy |
| 2002/0087101 A1 | 7/2002 | Barrick et al. |
| 2002/0133175 A1 | 9/2002 | Carson |
| 2002/0193797 A1 | 12/2002 | Johnson et al. |
| 2004/0019263 A1 | 1/2004 | Jutras et al. |
| 2004/0024311 A1 | 2/2004 | Quaid, III |
| 2004/0171929 A1 | 9/2004 | Leitner et al. |
| 2004/0230199 A1 | 11/2004 | Jansen et al. |
| 2004/0243148 A1 | 12/2004 | Wasielewski |
| 2005/0122616 A1 | 6/2005 | Hoelsaeter |
| 2005/0137599 A1 | 6/2005 | Masini |
| 2005/0216032 A1 | 9/2005 | Hayden |
| 2006/0122616 A1 | 6/2006 | Bennet et al. |

FOREIGN PATENT DOCUMENTS

| | | |
|---|---|---|
| WO | 2004030559 A1 | 4/2004 |
| WO | 2004046754 A2 | 6/2004 |
| WO | 2005023110 A1 | 3/2005 |

OTHER PUBLICATIONS

U.S. Appl No. 60/682,872, filed May 20, 2005, Jansen et al.
International Search Report. International Application No. PCT/CA2007/000464. Applicant: Orthosoft Inc. et al.

METHOD AND SYSTEM FOR TRACKING TOOLS IN COMPUTER-ASSISTED SURGERY

CROSS-REFERENCE TO RELATED APPLICATION

This patent application is a continuation of U.S. patent application Ser. No. 11/688,951, filed on Mar. 21, 2007, which claims priority on U.S. Provisional Patent Application No. 60/784,789, filed on Mar. 23, 2006, by the present applicants.

BACKGROUND OF THE INVENTION

1. Field of the Invention

The present invention relates to computer-assisted surgery and, more particularly, to the tracking of tools during orthopedic surgery.

2. Background Art

Orthopedic surgery is constantly evolving to lessen the effects of surgery on patients. In order to reduce the amount of post-surgical pain, new methods and tools have been developed to minimize the invasiveness of surgery.

Also, computer-assisted surgery is more commonly used in surgical rooms, so as to provide precision and accuracy to the surgeon. By way of computer-assisted surgery, position and orientation information is gathered during the surgical procedures, so as to provide to the surgeon real-time visual/digital data about bone alterations, tool navigation, and surgical parameters.

In parallel, apparatuses and methods have been developed to render orthopedic surgery minimally invasive. For instance, International Publication No. WO 03/068078, by Johnson et al., published on Aug. 21, 2003, describes an apparatus and method for minimally invasive total joint replacement. In that application, a bone-sculpting tool is attached directly to the femur, and an articular surface (i.e., acetabulum) between adjacent bones is sculpted with the joint between the bones reduced and one of the bones moving with respect to another.

In such minimally invasive applications, the tools used often have expandable geometries so as to be fitted within the small incisions. As tools have typically been tracked in computer-assisted surgery by trackers positioned directly on the tool, the tracking of tools in such minimally invasive applications is problematic, as, in some specific manipulations (e.g., bone sculpting of articular surfaces), there is a clear lack of space for trackers on the tools.

SUMMARY OF INVENTION

It is therefore an aim of the present invention to provide a novel system and method to track tools in computer-assisted surgery.

Therefore, in accordance with the present invention, there is provided a system for tracking a bone-altering tool in computer-assisted surgery, comprising: a first trackable reference secured to a first bone, with a first frame of reference being associated with the first trackable reference; a bone-altering tool securable to the first bone in a secured configuration; sensors to track at least the trackable reference for position and orientation; a position/orientation calculator connected to the sensor device to calculate a position and orientation of the first frame of reference; and an alteration parameter calculator associated with the position/orientation calculator to determine a position and orientation of the bone-altering tool in said secured configuration as a function of the position and orientation of the first frame of reference and of said secured configuration.

Further in accordance with the present invention, there is provided a method for tracking a tool secured to a bone/bone implant in computer-assisted surgery, comprising the steps of: tracking a first trackable reference secured to a first bone/bone implant for position and orientation; obtaining an interface relation of the tool secured to the first bone/bone implant; obtaining a model of the tool; and calculating at least a position of the tool secured to the first bone/bone implant as a function of the tracking of the first trackable reference, of the interface relation and of the model of the tool.

BRIEF DESCRIPTION OF THE DRAWINGS

Having thus generally described the nature of the invention, reference will now be made to the accompanying drawings, showing by way of illustration a preferred embodiment thereof and in which.

DESCRIPTION OF THE PREFERRED EMBODIMENTS

Figure 1:
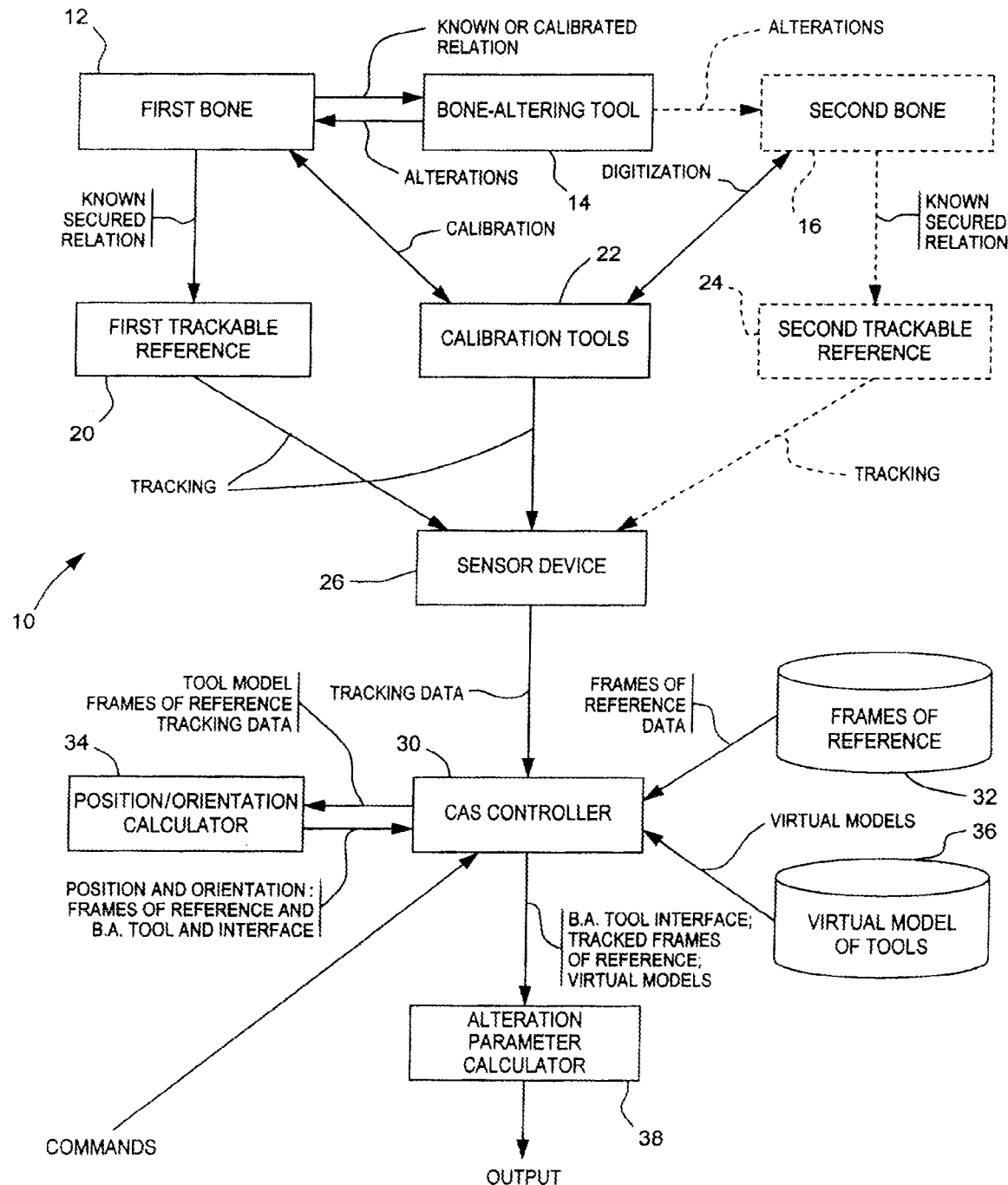
FIG. 1 is a block diagram of an alteration parameter calculator system constructed in accordance with a preferred embodiment of the present invention.

Referring now to FIG. 1, an alteration parameter calculator system in accordance with a preferred embodiment is generally shown at 10. The system 10 has controller, calculator and database components that are typically part of a computer-assisted surgery system (hereinafter CAS for computer-assisted surgery).

The system 10 is used in CAS to track tools and to provide alteration parameters associated with the alterations of a first bone 12 by a bone-altering tool 14, with the bone-altering tool 14 being anchored to the first bone 12 during the alterations. Alternatively, the bone-altering tool 14 may perform alterations on a second bone 16 while being anchored to the first bone 12. This technique is commonly used for sculpting/altering joint surfaces (such as the hip joint). The bone-altering tool 14 may be taken from a plurality of tools used to alter the bone surface of a bone (e.g., reamer), or used to insert and position an implant in a bone (e.g., cup impactor for acetabular implant).

The first bone 12 is provided with a first trackable reference 20. The first trackable reference 20 is secured to the first bone 12, and hence defines a first frame of reference of the first bone 12. Accordingly, the first trackable reference 20 is tracked such that information gathered with respect to the first bone 12 (e.g., landmarks, digitized surfaces, a coordinate system) is known with respect to the first frame of reference.

A calibration tool 22 is optionally used to determine the interface between the first bone 12 and the bone-altering tool 14, and to digitize information relating to the bones 12 and 14 with respect to the relevant frames of reference. This information may already be available, whereby the calibration tool 22 is optional.

The bone-altering tool 14 may alternatively be used to perform alterations on the second bone 16 while being anchored to the first bone 12, especially at the joint between the first bone 12 and the second bone 16. In such a case, a second trackable reference 24 is anchored to the second bone 16, so as to have a second frame of reference associated with the second bone 16. The second trackable reference 24 is tracked such that information gathered with respect to the second bone 16 (e.g., landmarks, digitized surfaces, a coordinate system) is known as a function of the second frame of reference.

Sensors 26 (i.e., a sensor device 26) are provided to track the first trackable reference 20, and, if applicable, the calibration tool 22 and the second trackable reference 24. It is contemplated to use various types of technologies for the sensors 26, such as optical, RF, magnetic sensors or the like. The sensors 26 are connected to the alteration parameter calculator system 10, such that the tracking data of the first trackable reference 20 and, if applicable, of the calibration tool 22 and the second trackable reference 24 is received and interpreted by the system 10.

The system 10 uses the CAS controller 30 of a CAS system. The CAS controller 30 receives commands during the course of surgery, and coordinates the tracking information received between the various components of the CAS system and of the alteration parameter calculator system 10. The CAS controller 30 is typically a processing unit of a computer.

Depending on the moment in surgery when the alteration parameter calculator system 10 is to be used, some information will already be available. In an embodiment, frames of reference associated with the first trackable reference 20 and, if applicable, the second trackable reference 24 are already known, as such frames of reference have been defined and used in prior steps for the navigation of tools during surgery. For instance, reference is made to International Publications No. WO 2004/030556 and WO 2004/030559, by Jansen et al., published Apr. 15, 2004, in which the definition and use of suitable frames of reference is described.

Accordingly, the frames of reference of the first bone 12 and, if applicable, of the second bone 16 are provided by the database of frames of reference 32, as well as associated data (e.g., landmarks, digitized surfaces, a coordinate system), as all information has been obtained prior to the steps of using the bone-altering tool 14.

The frame-of-reference data and the tracking data of the first trackable reference 20 and, if applicable, of the calibration tool 22 and the second trackable reference are received by a position/orientation calculator 34, which will calculate the position and orientation of the frames of reference in real time, as well as other information such as the interface between the first bone 12 and the bone-altering tool 14, from the tracking of the first trackable reference 20 and of the second trackable reference 24.

In some instances, the interface between the first bone 12 and the bone-altering tool 14 is a protruding portion of an implant. The above-referenced PCT publications by Jansen et al. have described methods to track the tools involved in the insertion of the implant in the bone (e.g., rasps), in such a way that the interface between the first bone 12 and the tool 14 is known as data associated with the frames of reference (and thus present in database 32).

Alternatively, the calibration tool 22 is used to calibrate the interface, by being connected in a known relation to the first bone 12 or protruding implant, or by digitizing points on a tool anchored to the bone 12, with respect to the first frame of reference. One calibration device suited to be used for the calibration of an implant interface is the device described in International Publication No. WO 2005/023110, by Amiot et al., as published on Mar. 17, 2005. Also, U.S. provisional application Ser. Nos. 60/682,872 and 60/682,852 describe digitization methods and devices which are suitable for use with the system 10. A virtual model of the tool 14 is obtained from the database 36 (e.g., resulting from a previous tool calibration), such that the position and orientation of the interface is calculable with respect to the first frame of reference by the position/orientation calculator 34, as a response from commands received by the CAS controller 30.

When the frames of reference are tracked in real time by the tracking of the first trackable reference 20 and, if applicable, of the second trackable reference 24, and the position and orientation of the interface between the first bone 12 and the bone-altering tool 14 is known with respect to the first frame of reference, the position and orientation of the tool 14 is calculable from the tracking of the first frame of reference. More specifically, a virtual model of the bone-altering tool 14 is provided by the database 36. The virtual model of the tool 14 is associated with the position and orientation of the interface between bone 12 and tool 14 with respect to the first frame of reference, such that a working surface of the tool 14 is known. Accordingly, as the position and orientation of the tool 14 is tracked, the effect of the tool 14 on the bone 12 or the bone 16 is calculable.

The alteration parameter calculator 38 calculates alteration parameters for alterations performed on the first bone 12 with the tracking of the tool 14 and the first frame of reference. Alternatively, if alterations are performed on the second bone 16, the alteration parameter calculator 38 calculates the alteration parameters with respect to the second frame of reference. In such a case, a digital model of the second bone 16, as obtained previously as described in the International Publications by Jansen et al., is provided by the database 32.

Figure 2:
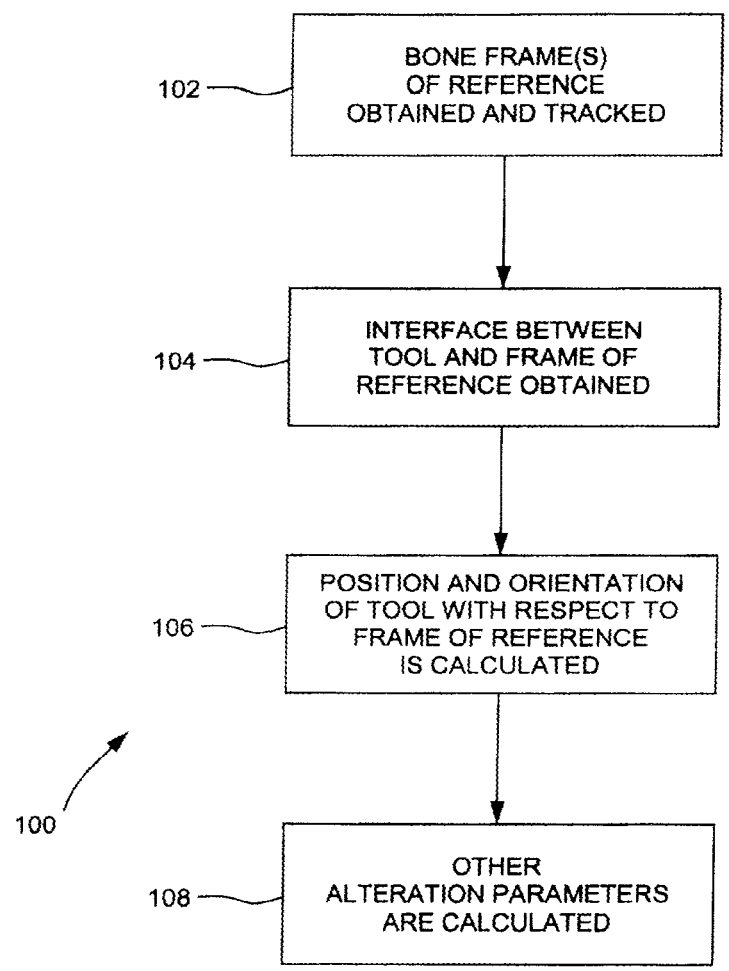
FIG. 2 is a flowchart of a method for calculating alteration parameters in accordance with another preferred embodiment of the present invention.

Referring concurrently to FIGS. 1 and 2, a practical example of the use of the alteration parameter calculator system 10 is described for hip joint replacement surgery, by method 100.

In Step 102, a frame of reference for the first bone is obtained and tracked. As described in the International Publications by Jansen et al., the first trackable reference 20 is secured to the femur (i.e., the first bone 12), and a frame of reference has been digitized, which frame of reference typically has a coordinate system with frontal, sagittal and transverse planes.

The method 100 is often performed once the frames of reference of the femur (with respect to the first trackable reference 20), and of the pelvis (i.e., second bone 16, with respect to the second trackable reference 24). Otherwise, the various steps described in the International Publications by Jansen et al. can be performed to obtain suitable frames of reference for the femur and for the pelvis, along with additional information associated with the frames of reference, such as digitized bone surfaces (e.g., acetabulum), position and orientation information data associated with implants inserted in the bones (e.g., femoral rasp/broach).

In Step 104, the interface between the bone-altering tool 14 and the femur is obtained with respect to the first frame of reference (i.e., associated with the first trackable reference 20 secured to the femur).

Figure 3:
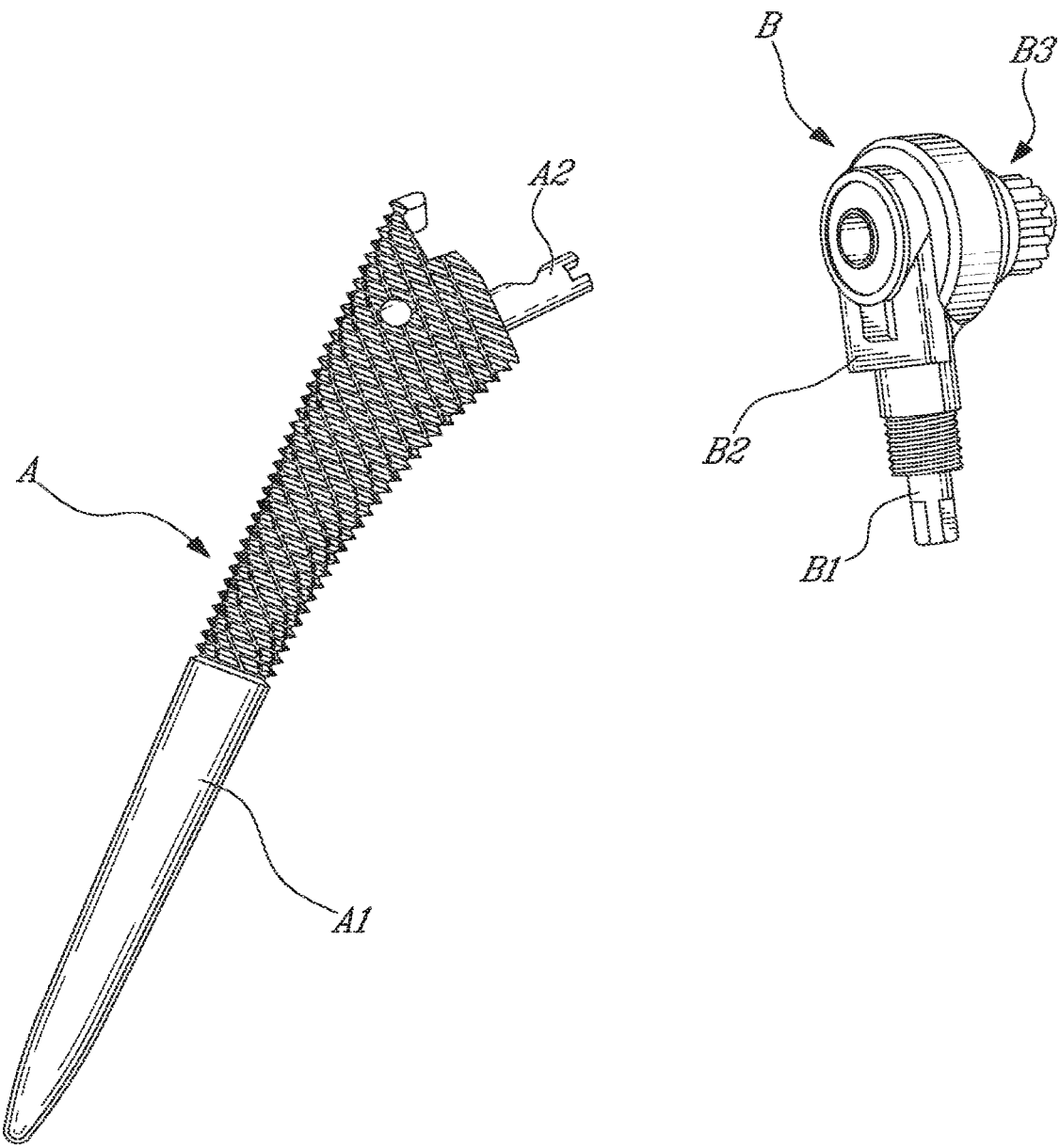
FIG. 3 is an exploded view of a rasp and bone-altering tool used with the system of FIG. 1.
Figure 4:
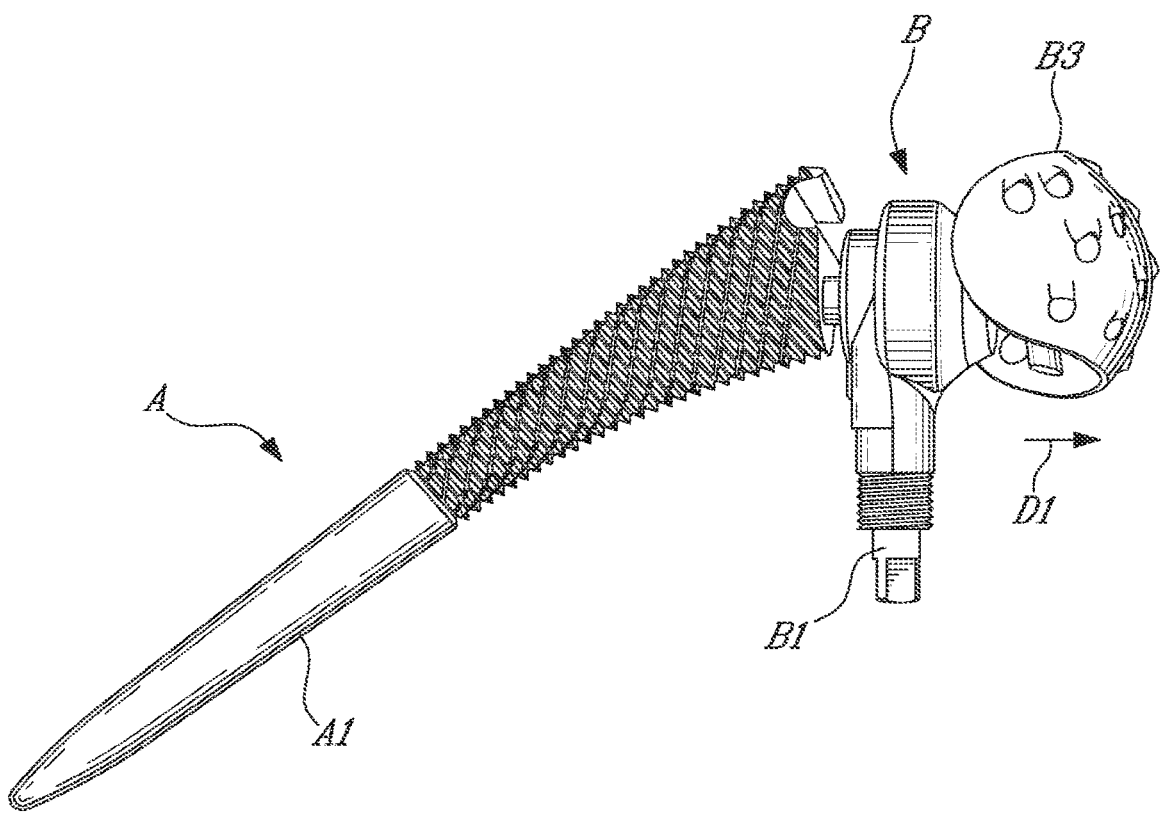
FIG. 4 is an assembly view of the rasp and bone-altering tool of FIG. 3.

Referring to FIG. 3, a femoral broach A has a body A1 and a ball head connector A2 (i.e., the neck). The ball head connector A2 will be used with the bone-altering tool (FIG. 1), which is represented in FIG. 3 by reamer B. The reamer B has a driveshaft B1, at the end of which a connector socket B2 is positioned opposite an actuator head B3. As shown in FIG. 4, the broach A and the reamer B are interconnected by the mating engagement of the ball head connector A2 in the connector socket B2.

In computer-assisted surgery, the insertion of a femoral implant (rasp/broach) is frequently tracked with respect to the femoral frame of reference (e.g., by tracking the impacting tool), such that a position and orientation of the implant is known. In such a case, the position and orientation of the ball head connector A2 is known with respect to the femoral frame of reference.

Alternatively, if it is not available, the position and orientation data of the interface is readily obtained by digitizing the surface of the interface, for instance using a positioning tool having a socket mated to the ball head connector A2 or a registration pointer.

In Step 106, a calculation and tracking of a position and orientation of a working surface of the tool is performed. A virtual model of the tool 14/reamer B (including the relation between the tool 14 and the bone/implant) is associated with the first frame of reference through the tracking of the first trackable reference 20 on the femur, by knowing the position and orientation of the interface between bone and tool, during this calculation. This calculation is performed by the alteration parameter calculator 38 (FIG. 1).

In the case of hip-joint surgery, the reamer B of FIG. 4 extends a known distance along direction Dl. This translational degree of freedom is provided in order to minimize the size of the reamer B for being fitted in small incisions, while expanding to simulate the size of a finished implant/femoral neck when actuated to ream the surface of the acetabulum from its anchored position on the femur/femur implant.

Accordingly, in Step 108, alterations (i.e., alteration parameters) on the first bone 12 or the second bone 16 are calculated as they are performed. The calculations are performed by the alteration parameter calculator 38 from the tracking of the working surface of the tool 14 through the first frame of reference, and from the tracking of bone surface information associated with either the first trackable reference 20 (first bone 12) or the second trackable reference 24 (second bone 16).

In the case of hip-joint surgery, the tracked bone surface information relates to the geometry of the acetabulum (second bone 16), which data has been obtained and is part of the data associated with the second frame of reference through the database 32. As the position and orientation of the working surface of the reamer B is tracked as a function of the first trackable reference 20, the effect of the reamer B on the acetabulum is calculated by relating the tracking of the second frame of reference (and associated acetabulum surface data) with the position and orientation of the working surface of the reamer B.

Therefore, the alteration parameter calculator system 10 calculates the position and orientation of a bone-altering tool (e.g., 14) from the tracking of a trackable reference (e.g., 20) secured to a bone (e.g., 12) upon which the bone-altering tool is also secured during actuation of the tool.

Another alteration parameter that may be calculated is the amount of bone material removed from the bone on which the tool 14 is secured, or the amount of bone material removed from the bone adjacent to the tool 14 (as is the case for the hip-joint surgery described above). In such a case, the other bone (i.e., bone 16) is tracked for position and orientation, and relevant bone data is available (e.g., landmarks, digitized surfaces, a coordinate system).

Also, in the case of hip-joint surgery the anteversion and inclination of the actuation axis of the tool 14, both as a function of the acetabular coordinate system (from a tracking of the second reference 24), can be given numerically (e.g., in degrees) to guide the surgeon in the reaming. More precisely, the anteversion is calculated as the angle between an intersection of the acetabular frontal plane and transverse plane and the projection of the axis of the reamer on the acetabular transverse plane, and the inclination is the angle between the reamer axis and a cranial-caudal axis (y) on the sagittal plane of the acetabular coordinate system.

Also, the distances between the current and the digitized centers of rotation can be displayed. Therefore, the surgeon is guided during the use of the bone-altering tool 14 so as to position the pelvic implant to a given position of the center of rotation thereof, and to a given orientation (with respect to anteversion and inclination) to provide a maximal range of motion and stability of the leg.

In the case of hip-joint surgery, a femoral target height is calculable as a desired position for the femoral center of rotation, and is calculated as follows: (target height)= $(\Delta_{PELVIC\ COR})-(\text{initial } \Delta_{LL})$, where $(\Delta_{PELVIC\ COR})$ is the deviation of the implant center of rotation with respect to the digitized acetabular center of rotation, in cranial-caudal (y) direction (with a cranial deviation having a positive value), and (initial $\Delta_{LL}$) is the initially acquired limb length discrepancy.

Also in the case of hip-joint surgery, the anteversion of the femoral implant as calculated from the tracked rasp/broach can be displayed numerically (e.g., in degrees) based on the femoral coordinate system obtained in Step 102. It is represented by the angle between the intersection of the frontal plane and the transverse plane and a projection of the neck axis (anticipated for the femoral implant) onto the transverse plane.

Another guiding parameter to be provided to the surgeon is the distance between the previous femoral center of rotation and the current femoral center of rotation. The current femoral center of rotation is calculated as a function of the femoral implant geometry (e.g., the ball head size) and the tracking of the rasp/broach. The distance can be given in X, Y and Z values (e.g., in mm) according to the femoral coordinate system.

Another guiding parameter to be provided to the surgeon in hip-joint surgery is the current leg-length discrepancy. The current leg-length discrepancy, (current $\Delta_{LL}$), is calculated as follows: (current $\Delta_{LL}$)= (initial $\Delta_{LL}$)−($\Delta_{PELVIC\ COR}$)+($\Delta_{FEMUR\ COR}$), where ($\Delta_{FEMUR\ COR}$) is the Y value calculated above, and where ($\Delta_{PELVIC\ COR}$) and (initial $\Delta_{LL}$) have been described above. The current leg-length discrepancy can be displayed by the CAS system as an overall leg length, or as a relative value between leg lengths, with the value 0 representing legs of equal length.

Another guiding parameter used in hip-joint surgery is the offset of the femoral implant. The offset is the distance between the acetabular center of rotation and the axis of the implant (i.e., the anatomical axis of the femur as defined previously) on the transverse plane, and is thus directly related to the size of the femoral implant. It is pointed out that a type of femoral implant contemplated for the above-described method 100 can be provided in various sizes, and a size of femoral implant can have various femoral centers of rotation along the neck of the implant. A proper identification of the size of the femoral implant must therefore be provided as it will have an effect on both the offset and the limb length.

The invention claimed is:

1. A system for tracking alterations to an acetabulum of a pelvis in computer-assisted surgery, comprising:
    a first trackable reference secured to a femur;
    a tool having a working surface to alter the acetabulum, the tool configured to be in a secured relation with the femur;
    at least one sensor to track at least the first trackable reference;
    a computer-assisted surgery controller for digitizing a relation of the tool relative to the first trackable reference using a virtual model of the tool, while the tool is in said secured relation, for tracking the working surface of the tool as a function of the tracking of the first trackable reference, using said relation and the virtual model of the tool, and for outputting real-time data pertaining to an alteration of the acetabulum by the working surface of the tool, using a virtual model of the pelvis.

2. The system according to claim 1, further comprising a second trackable reference secured to the pelvis, the computer-assisted surgery controller calculating at least one parameter associated with alterations to the pelvis by the working surface of the tool in the secured relation as a function of a tracking of the pelvis with the second trackable reference.

3. The system according to claim 2, further including a calibration tool to digitize a model of the pelvis with respect to the second trackable reference, with said at least one parameter being alterations to the acetabulum calculated from the model of the pelvis.

4. The system according to claim 1, wherein the secured relation is represented by position and orientation data associated with an interface between the femur and the tool, and with the virtual model of the tool.

5. The system according to claim 4, wherein the virtual model of the tool is known preoperatively.

6. The system according to claim 4, further including a calibration tool to digitize said position and orientation data associated with said interface between the femur and the tool.

7. The system according to claim 1, further including a calibration tool to digitize the virtual model of the tool.

8. The system according to claim 1, wherein the tool is a reamer.

9. The system according to claim 1, further including a broach implanted in the femur, the tool being a reamer securable to the broach in the secured relation.

10. A method for tracking alterations to an acetabulum of a pelvis, comprising:
    tracking a femur by a first trackable reference on the femur, with a tool being in a secured relation on the femur, the tool having a working surface to alter the acetabulum;
    obtaining a virtual model of the tool including the working surface;
    digitizing a relation of the tool relative to the first trackable reference using the virtual model of the tool, while the tool is in said secured relation;
    tracking the working surface of the tool as a function of the tracking of the first trackable reference, using said relation and the virtual model of the tool; and
    outputting data pertaining to an alteration of the acetabulum during alteration by the working surface of the tool, using a virtual model of the pelvis.

11. The method according to claim 10, further including tracking the pelvis via a second trackable reference on the pelvis while tracking the working surface of said tool, and calculating an alteration performed in the acetabulum using the tracking of the tool and the tracking of the femur.

12. The method according to claim 11, further including digitizing a surface of the acetabulum to obtain the virtual model of the pelvis.

13. The method according to claim 10, wherein digitizing the relation of the tool relative to the first trackable reference is performed by digitizing a surface of the femur and/or of a bone implant on the femur with respect to the first trackable reference.

14. The method according to claim 10, wherein obtaining the virtual model of the tool involves receiving the model created preoperatively.

15. The method according to claim 14, wherein obtaining the virtual model of the tool includes registering points on the tool intraoperatively.

16. The method according to claim 10, wherein obtaining the virtual model of the tool includes registering points on the tool intraoperatively.

17. The method according to claim 10, wherein the method is performed with the tool being a reamer.

18. The method according to claim 17, wherein the method is performed with a resected femur, and with the reamer being mounted to a broach implanted in the resected femur.

* * * * *